United States Patent [19]
Reilly

[11] Patent Number: 5,281,423
[45] Date of Patent: Jan. 25, 1994

[54] USE OF HYDRIODIC ACID AS AN APHRODISIAC

[76] Inventor: Susann R. Reilly, 300 Commercial St., Apt. 412, Boston, Mass. 02109

[21] Appl. No.: 862,454

[22] Filed: Apr. 2, 1992

[51] Int. Cl.$^5$ ............................................. A61K 33/36
[52] U.S. Cl. ..................................................... 424/667
[58] Field of Search ........................................... 424/662

[56] References Cited
PUBLICATIONS

McEvoy et al.; AHFS, Drug Information pp. 1398–1399 (1987).
Waddell and Ibach, Indian J. Pharm. Sci., 51(3):79–82 (1989).
Buffum, Journal of Psychoactive Drugs, 14(1–2):5–44 Jan.–Jun. 1982.
The Merck Index, Tenth Edition, 692, 696–697, 1983.

Primary Examiner—Allen J. Robinson
Attorney, Agent, or Firm—Hamilton, Brook, Smith & Reynolds

[57] ABSTRACT

This invention relates to the use of hydriodic acid in an aqueous solution as an aphrodisiac to heighten sexual desire.

4 Claims, No Drawings

USE OF HYDRIODIC ACID AS AN APHRODISIAC

BACKGROUND OF THE INVENTION

From the dawn of recorded history many substances have been used for the purpose of sexual enhancement. Some of these have known success and their reputations have been passed down through the millennia. Even though none of these substances have survived the rigors of scientific scrutiny the pursuit for an aphrodisiac continues. As long as humans place value on optimal sexual functioning, there will be a demand for sex-enhancing drugs.

SUMMARY OF THE INVENTION

This invention relates to the use of hydriodic acid in an aqueous solution as an aphrodisiac to heighten sexual desire.

DETAILED DESCRIPTION OF THE INVENTION

This invention is based upon the discovery that an aqueous solution of hydriodic acid (hydriodic solution) can heighten sexual desire and, as such, can be used as an aphrodisiac.

Hydriodic acid is also known as anhydrous hydriodic acid, hydrogen iodide, hydrogen monoiodide or hydriodic. At normal temperature, hydriodic acid is a colorless and nonflammable gas. See The Merck Index, Merck & Co., Inc. (Tenth Edition 1983).

The hydriodic acid solution of the present invention consists of hydriodic acid in purified water and dextrose.

It has now been discovered that an aqueous solution of hydriodic acid has aphrodisiac activity as confirmed through its use by a female human. After the oral administration of the hydriodic acid solution, an aphrodisiac effect was experienced by said female.

The term "aphrodisiac" or "heightened sexual desire", for purposes of the present invention, refers to the following physical manifestations of ingesting the hydriodic solution, increased vaginal secretion, clitoral swelling, nipple erection, contraction of vaginal musculature and a general tingling sensation.

The invention will be further illustrated by the following non-limiting Exemplification:

EXEMPLIFICATION

Hydriodic acid solution was purchased from Eli Lilly and Company, of Indianapolis, Ind., referred to as hydriodic acid syrup. The hydriodic acid syrup is prepared by mixing 140 ml of hydriodic acid with 550 ml of purified water and dissolving 450 g of dextrose into the mixture.

The solution was orally administered to a female human 52 years age, weighing 165 lb pounds. About 0.5–3 teaspoons of the hydriodic syrup was placed into 8 ounces tap water and then ingested. An aphrodisiac effect, as defined above, was experienced within approximately 24 hours.

It is understood that higher or lower amounts and concentrations of the hydriodic solution would be used for heavier or lighter subjects as in the purview of one skilled in the art.

It should be, as well, understood that other types of administration of the hydriodic solution may be used, such as topical administration.

EQUIVALENTS

Those skilled in the art will recognize, or be able to ascertain, using no more than routine experimentation many equivalents to the specific embodiments of the invention described herein. Such equivalents are intended to be encompassed by the following claims:

I claim:

1. A method of heightening sexual desire of an adult human female comprising administering to an adult human female in need of said treatment, an effective amount of hydriodic acid syrup, comprising hydriodic acid, water and dextrose.

2. A method of claim 1 wherein the hydriodic acid syrup comprises 140 ml of hydriodic acid, 550 ml of water and 450 g of dextrose.

3. A method of claim 2 wherein the effective amount of hydriodic acid syrup is approximately 0.5–3 teaspoons of hydriodic acid syrup.

4. A method of claim 3 wherein the effective amount of hydriodic syrup is added into approximately 8 oz. of water before administration.

* * * * *